US012766339B2

(12) United States Patent
Kang et al.

(10) Patent No.: US 12,766,339 B2
(45) Date of Patent: Oct. 20, 2026

(54) DISINFECTION DEVICE BASED ON LIGHT IN PROXIMITY TO SYRINGE

(71) Applicants: PUKYONG NATIONAL UNIVERSITY INDUSTRY-UNIVERSITY COOPERATION FOUNDATION, Busan (KR); KOSIN UNIVERSITY INDUSTRY-ACADEMIC COOPERATION FOUNDATION, Busan (KR)

(72) Inventors: Hyun Wook Kang, Busan (KR); Hyung Shin Lee, Busan (KR)

(73) Assignees: PUKYONG NATIONAL UNIVERSITY INDUSTRY-UNIVERSITY COOPERATION FOUNDATION, Busan (KR); KOSIN UNIVERSITY INDUSTRY-ACADEMIC COOPERATION FOUNDATION, Busan (KR)

( * ) Notice: Subject to any disclaimer, the term of this patent is extended or adjusted under 35 U.S.C. 154(b) by 418 days.

(21) Appl. No.: 18/386,344

(22) Filed: Nov. 2, 2023

(65) Prior Publication Data

US 2024/0173563 A1 May 30, 2024

(30) Foreign Application Priority Data

Nov. 24, 2022 (KR) ........................ 10-2022-0159260

(51) Int. Cl.

*A61N 5/06* (2006.01)
*A61M 5/158* (2006.01)
*A61M 25/00* (2006.01)

(52) U.S. Cl.

CPC ........... *A61N 5/0624* (2013.01); *A61M 5/158* (2013.01); *A61M 2005/1581* (2013.01);

(Continued)

(58) Field of Classification Search

CPC .................... A61M 5/42; A61M 5/422; A61M 2005/1585; A61M 2005/1581;

(Continued)

(56) References Cited

U.S. PATENT DOCUMENTS

| | | | |
|---|---|---|---|
| 10,307,612 | B2 | 6/2019 | Barneck et al. |
| 11,020,570 | B2 | 6/2021 | Laudenslager et al. |

(Continued)

FOREIGN PATENT DOCUMENTS

| | | | |
|---|---|---|---|
| KR | 10-2009-0018592 | A | 2/2009 |
| KR | 10-2009-0055416 | A | 6/2009 |

(Continued)

OTHER PUBLICATIONS

Office Action from corresponding Korean Patent Application No. 10-2022-0159260, dated Oct. 26, 2023.

*Primary Examiner* — Nilay J Shah

(74) *Attorney, Agent, or Firm* — Harness, Dickey & Pierce, P.L.C.

(57) ABSTRACT

The present disclosure relates to a disinfection device based on light in close proximity to a syringe. A light-based disinfection device of the present disclosure configured to achieve disinfection of a skin tissue by placing light in close proximity to an injection needle for drug injection, the light-based disinfection device including: a light delivery catheter comprising one end portion connected to a control device and the other end portion configured to direct light from a light source controlled by the control device toward skin tissue; a needle catheter comprising one end portion connected to a drug container and to accommodate a cath- (Continued)

eter line that supplies a drug, and the other end portion configured to accommodate an injection needle that receives the drug from the catheter line and injects the drug into a patient's body; and a coupler configured to couple the light delivery catheter and the needle catheter in parallel to each other in a longitudinal direction.

17 Claims, 15 Drawing Sheets

(52) U.S. Cl.
CPC ............... *A61M 2005/1585* (2013.01); *A61M 2005/1587* (2013.01); *A61M 2025/0092* (2013.01); *A61M 2205/051* (2013.01); *A61N 2005/0626* (2013.01); *A61N 2005/0666* (2013.01)

(58) Field of Classification Search
CPC .... A61M 2005/1587; A61M 2205/051; A61N 5/0624; A61L 27/3839
See application file for complete search history.

(56) References Cited

U.S. PATENT DOCUMENTS

| | | | | |
|---|---|---|---|---|
| 2003/0018373 | A1 | 1/2003 | Eckhardt et al. | |
| 2003/0153961 | A1* | 8/2003 | Babaev ................ | A61B 18/203 607/89 |
| 2004/0193218 | A1* | 9/2004 | Butler ................... | A61M 3/022 607/1 |
| 2010/0152644 | A1* | 6/2010 | Pesach ............. | A61M 5/14244 604/20 |
| 2013/0267888 | A1* | 10/2013 | Rhodes ............. | A61M 25/0017 604/21 |
| 2019/0374668 | A1* | 12/2019 | Kopperschmidt ........ | A61L 2/10 |
| 2020/0054842 | A1* | 2/2020 | Thawer ................... | A61M 5/42 |

FOREIGN PATENT DOCUMENTS

| | | | |
|---|---|---|---|
| KR | 10-2015-0010467 | A | 1/2015 |
| KR | 10-2021-0061378 | A | 5/2021 |
| KR | 10-2022-0043332 | A | 4/2022 |
| KR | 10-2415201 | B1 | 6/2022 |

* cited by examiner

DISINFECTION DEVICE BASED ON LIGHT IN PROXIMITY TO SYRINGE

CROSS-REFERENCE TO RELATED APPLICATION

This application is based on and claims priority under 35 U.S.C. 119 to Korean Patent Application No. 10-2022-0159260, filed on Nov. 24, 2022, in the Korean Intellectual Property Office, the disclosure of which is herein incorporated by reference in its entirety.

FIELD

The present disclosure relates to a light-based disinfection device. In particular, the present disclosure relates to a device that is capable of disinfecting a site around a skin tissue where a drug is injected based on light, such as laser beams, near-ultraviolet rays, visible rays, or near-infrared rays during, in close proximity to an injection needle for gradual drug injection into a patient's body, hemodialysis, or the like drug injection.

BACKGROUND

Injection needles are used for gradual drug injection into a patient's body, such as IV injection or injection using an implantable central venous catheter, or for hemodialysis, wherein disinfection of the injection needle inserted into the skin is essential to prevent the risk of inflammatory infection such as bacterial infection.

For example, during anticancer treatment, an implantable central venous tube (chemoport) is inserted into the patient's upper left subcutaneous fat layer for repeated administration of anticancer drugs. The implantable central venous catheter has the advantage of allowing intravenous injection without securing a blood vessel and allowing the patient to move freely during the injection of drugs, but caution is required as bacterial infection may occur. In particular, since disinfection is required when using needles and periodic needle replacement is required, an additional disinfection process is necessary to prevent the risk of inflammatory infection for safe anticancer treatment.

As related prior documents, U.S. Pat. No. 10,307,612 (issued on Jun. 4, 2019), U.S. Pat. No. 11,020,570 (issued on Jun. 1, 2021), and the like may be referred to.

SUMMARY

Accordingly, the present disclosure was made to solve the above-mentioned problems, and the present disclosure provides a light-based disinfection device that is capable of minimizing and preventing infection by broadly and uniformly radiating light, such as laser beams, near-ultraviolet rays, visible rays, and near-infrared rays, to an area around a skin tissue where the drug is injected in close proximity to an injection needle for administering an anticancer drug or the like during drug injection to ensure that the site where the skin tissue and the injection needle are in contact with each other and the surroundings of the site are disinfected.

First, the features of the present disclosure may be summarized as follows. In view of the foregoing, a light-based disinfection device according to an aspect of the present disclosure configured to achieve disinfection of a skin tissue by placing light in close proximity to an injection needle for drug injection, the light-based disinfection device may include: a light delivery catheter including one end portion connected to a control device and the other end portion configured to direct light from a light source controlled by the control device toward skin tissue; a needle catheter including one end portion connected to a drug container and to accommodate a catheter line that supplies a drug, and the other end portion configured to accommodate an injection needle that receives the drug from the catheter line and injects the drug into a patient's body; and a coupler configured to couple the light delivery catheter and the needle catheter in parallel to each other in a longitudinal direction.

The light-based disinfection device may be used to insert the injection needle of the needle catheter into a chemoport inserted into a patient's body, and may also be used for the administration or the like of any injection drug that takes a certain amount of time, from an IV injection liquid container or the like.

The light source may be an optical element disposed at the other end portion of the light delivery catheter to be connected to control lines and power lines extending from the control device, and may be an optical fiber that delivers light generated by the control device and has an end portion disposed at the other end portion of the light delivery catheter.

The light source may be configured to emit laser beams, near-ultraviolet rays, visible rays or near-infrared rays as continuous or pulsed light with a wavelength ranging from 400 nm to 3000 nm and an energy density of 0.01 to 10 $J/cm^2$, and power density of 0.01 to 10 $W/cm^2$.

The light source may be configured to be controlled by the control device in terms of one or more disinfection conditions from among a light intensity, a light emission time, selection of a continuous or pulsed light delivery method, a light output energy or power range, selection of a light distribution, and a number of times of disinfection operation.

The light-based disinfection device may further include a user terminal connected to the control device in a wired or wireless manner, wherein the user terminal may be configured to control an operation of the light source by transmitting the disinfection conditions or a schedule including one or more lists of the disinfection conditions stored in advance to the control device, to store information on the controlled disinfection conditions or schedule which have been transmitted to the control device and under which the operation of the light source has been controlled, and to provide the information in response to a user's inquiry request.

The light may be radiated toward the end portion of the injection needle at an angel of 30 to 90 degrees by the other end portion of the light delivery catheter.

The light delivery catheter may further include a light diffusion prevention film at the other end portion to block light reflected or scattered rearward when the light from the light source is radiated to the skin tissue.

The light diffusion prevention film may be configured to be rotatable or bendable.

The light diffusion prevention film may include a coating film configured to reflect or scatter light.

The light diffusion prevention film may include a coating film configured to absorb light.

The coupler may include a catheter connector configured to be placed and rotated around the light delivery catheter or the needle catheter.

The coupler may include a tube configured to wrap bodies of the light delivery catheter and the needle catheter to place the bodies of the light delivery catheter and the needle catheter therein.

When the end portion of the injection needle at the other end portion of the needle catheter is bent and directed in a different direction with respect to the longitudinal direction, the other end portion of the light delivery catheter may extend in an extension direction without being bent.

When the end portion of the injection needle at the other end portion of the needle catheter is bent and directed in a different direction with respect to the longitudinal direction, the other end portion of the light delivery catheter may be bent in the other direction to direct the light toward the skin tissue.

When the injection needle at the other end portion of the needle catheter extends in an extension direction without being bent, the light source disposed at the other end portion of the light delivery catheter may be configured to be rotatable or bendable such that a light radiation direction can be changed.

The other end portion of the light delivery catheter may include a light radiation portion having a hole for inserting the injection needle, and a plurality of light sources controlled by the control device may be arranged around the hole of the light radiation portion.

The light-based disinfection device may further include a light radiation regulation portion configured to diffuse or scatter the light from the other end portion of the light delivery catheter to regulate the light to have a predetermined light radiation range, light radiation intensity, or light distribution on the skin tissue.

With the light-based disinfection device of the present disclosure, it is possible to minimize and prevent infection by radiating light such as laser beams, near-ultraviolet rays, visible rays, or near-infrared rays widely and uniformly around the skin tissue in close proximity to the injection needle during drug injection to ensure that the site where the skin tissue and the injection needle are in contact with each other and the surroundings of the site are disinfected. For example, when administering an anticancer drug by inserting an injection needle into the chemoport, the needle insertion site and the surroundings of the needle insertion site can be disinfected by applying the light-based disinfection device of the present disclosure in the vicinity of the needle, and the light-based disinfection device can also be applied to the surrounding transplanted tissues, which allows for extensive optical disinfection. In addition, infection around the chemoport can be prevented by performing periodic non-contact optical disinfection by applying the light-based disinfection device of the present disclosure during or after anticancer drug administration. In addition, it is expected that the light-based disinfection device of the present disclosure can be used in various implantable devices or the like.

BRIEF DESCRIPTION OF THE DRAWINGS

The accompanying drawings, which are included as a part of the detailed description to help the understanding of the present disclosure, provide embodiments of the present disclosure and illustrate the technical spirit of the present disclosure together with the detailed description, in which.

DETAILED DESCRIPTION

Figure 1:
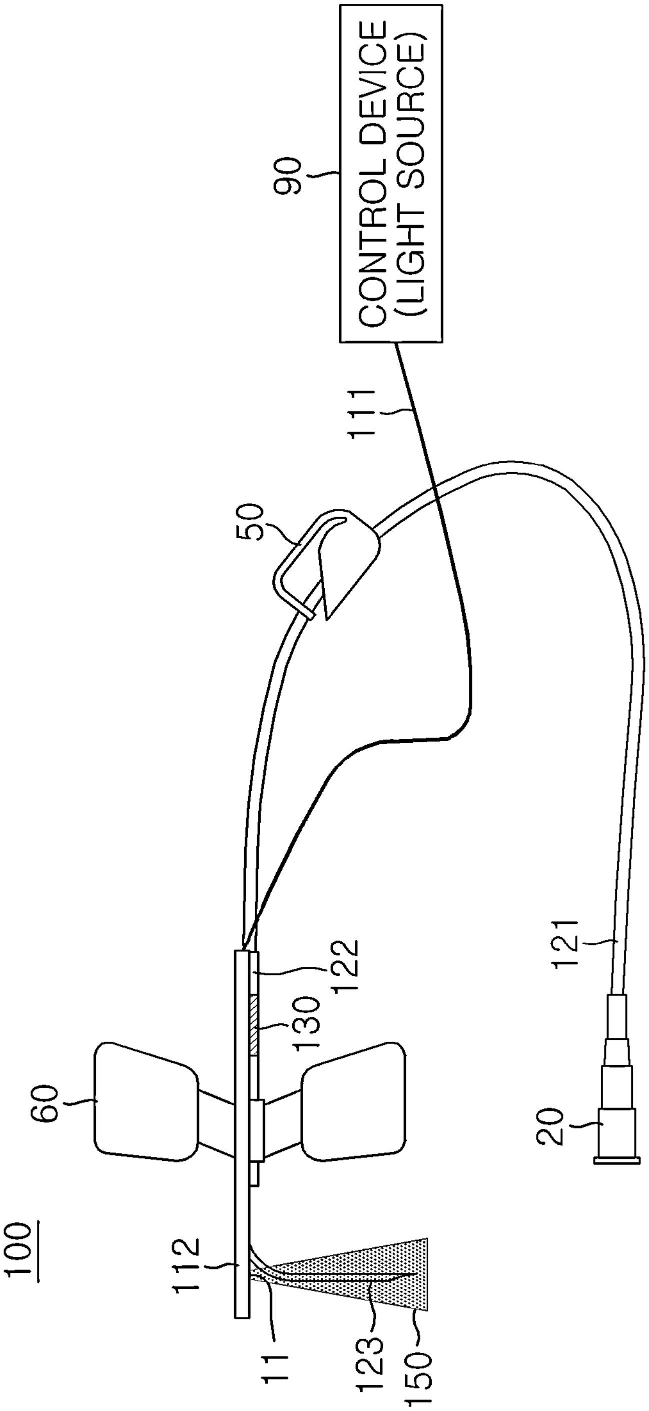
FIG. 1 is a conceptual view of a light-based disinfection device of the present disclosure.

Hereinafter, the present disclosure will be described in detail with reference to the accompanying drawings. Herein, like components in each drawing are denoted by like reference numerals if possible. In addition, detailed descriptions of already known functions and/or configurations will be omitted. In the following description, components necessary for understanding operations according to various embodiments will be mainly described, and descriptions of elements that may obscure the gist of the description will be omitted. In addition, some elements in the drawings may be exaggerated, omitted, or schematically illustrated. The size of each component does not entirely reflect the actual size, and therefore, the descriptions provided herein are not limited by the relative sizes or spacings of the components drawn in each drawing.

In describing the embodiments of the present disclosure, when it is determined that a detailed description of the known technology related to the present disclosure may unnecessarily obscure the subject matter of the present disclosure, the detailed description will be omitted. In addition, terms to be described later are defined in consideration of functions in the present disclosure and may vary according to the intention, custom, or the like of a user or operator. Therefore, the definitions of the terms should be made based on the description throughout this specification. Terms used in the detailed description are only for describing the embodiments of the present disclosure, and should not be treated as limiting. Unless expressly used otherwise, an expression in the singular form includes the meaning in the plural form. In this description, expressions such as "including" or "comprising" are intended to indicate any features, numbers, steps, operations, elements, or some or combinations thereof, and should not be construed to exclude the existence or possibility of one or more other features, numbers, steps, operations, elements, or some or combinations thereof.

In addition, terms such as "first" and "second" may be used to describe various components, but the components are not limited by the terms, and these terms are only used for the purpose of distinguishing one component from another.

First, a description will be made of the principle of a delivery device of the present disclosure in which diseases are treated by inducing stimulation, destruction, incision, or coagulation of a lesional tissue with cancer or other symptoms in a digestive organ system by radiating light, such as laser beams, near-ultraviolet rays, visible rays, or near-infrared rays to a target lumen or tubular lesion tissue.

<Principle of Optical Disinfection>

Low-level laser therapy induces stimulation, destruction, incision, or coagulation of lesion tissue and includes low-power therapy, photodynamic therapy, photothermal therapy, and the like. The low-level laser therapy is based on a treatment principle of stimulating cell activity and vitality without damaging issue by a non-invasive and non-thermal method by generally radiating light with a wavelength ranging from 400 to 3000 nm at an intensity equal to or less than 100 J/cm$^2$. Such low-level laser therapy is capable of achieving clinical effects by radiating a predetermined level of electromagnetic energy to stimulate or inhibit cellular functions. Here, light sources of near-ultraviolet rays, visible rays, near-infrared rays, and the like may be applicable for pain relief, inflammation, swelling, tissue necrosis prevention, tissue recovery, and the like. The low-level laser therapy may maximize the treatment effect depending on the exact wavelength required for treatment, appropriate power, distribution of electromagnetic energy, and control of the amount of electromagnetic energy. In addition, LED chips may be used to generate electromagnetic energy, and the power varies depending on the wavelength, wherein, in the LED chips that have been developed so far, the near-ultraviolet region of the 400 nm band has an optical output of 20 mW, the 850 to 900 nm band has an optical output of 10 mW or more, and the 600 to 700 nm band, which is effective in relieving pain, has an average power of up to 40 mW.

The typical initial response of cells to light radiation is an increase in adenosine triphosphate (ATP) and calcium ions. ATP and calcium ions increase, and the energy generated at this time may increase mitochondria potential, activate second messengers (CAMP, cGMP, heat shock protein, and the like), and adjust the amount of generation of reactive oxygen species (ROS). In particular, differentiation, migration, and proliferation of normal cells may be induced by 7 regulating the amount of ROS, and in damaged states of the tissue, antioxidant effects and inflammation-relieving effects may be induced by reducing the amount of ROS.

The mechanism of low-level lasers on cellular function relies on photon absorption by cytochrome c (CCO), which plays an important role in oxygen metabolism and adenosine triphosphate (ATP) production. Low-level lasers may increase the concentration of cytochrome c, which may lead to a longer-term metabolic effect, resulting in an effect of improving cellular oxygen metabolism. Low-level lasers may adjust molecule-dependent biological processes such as growth factor production, cell proliferation, migration, and cell death. Fibroblasts, which are the main mechanism of fibrosis, are transformed into myofibroblasts by growth factors during a wound healing process. During this process, excessive expression of growth factors leads to abnormal expression of extracellular matrix and formation of collagen, causing fibrosis. The treatment principle of red light in the 600 to 800 nm wavelength range is to reduce the expression of induced growth factors that cause stenosis, that is, fibrotic disease. Blue light in the 400 nm wavelength range functions to directly generate reactive oxygen species (ROS) and photo-stimulate flavin attached to the complex of mitochondrial electron transport chain, and may induce and adjust changes in cytokines, growth factors, and inflammatory mediators that promote inflammatory responses.

Laser radiation with red light not only has the effect of normalizing excessive fibrotic activity in metastasis-induced fibroblasts by regulating growth factors, but also has an anti-inflammatory effect by regulating prostaglandin E2 production and cyclooxygenase (COX) m-RNA expression. In addition, the laser in the 600 to 800 nm wavelength range reduces inflammatory responses based on the mechanism of inhibiting intracellular reactive oxygen species in blood pressure via the action of peroxide-removing enzymes and catalase enzyme activity and changing calcium (Ca2) mobilization. The blue light laser in the 400 nm wavelength ranges may perform functions such as directly generating reactive oxygen species (ROS) and optically stimulating flavins attached to complexes of mitochondrial electron transport chains, and induces and regulates changes in cytokines, growth factors, and inflammatory mediators that promote inflammatory responses. The infrared laser in the 900 nm wavelength range has an anti-inflammatory effect that alleviates inflammatory responses based on the mechanism of reducing the immune response to allergens by suppressing histamine release. In addition, an infrared laser, with its high penetration capability, has effects on cell proliferation, neovascularization, collagen accumulation, and re-epithelialization in a wound healing process.

Photodynamic therapy injects a photosensitizer (or photosensitizing agent) into a patient's body to accumulate the same in the patient's body, and uses light energy to destroy diseases or tumors. When the photosensitizer absorbs light energy, reactive oxygen (reactive singlet oxygen) is generated, which directly causes necrosis or death of cells and eliminates diseases or tumors. In the photodynamic therapy, the wavelength range of 600 to 800 nm is frequently used, and light energy is radiated several days after the photosensitizer is administered. The effect of photodynamic therapy varies depending on the type and dosage of the photosensitizer, the drug-light interval, wavelength (nm), radiation intensity (mW), radiation energy (J), and the number of times of radiation. Photodynamic therapy is a photochemical process that does not generate heat and has little impact on surrounding tissues, so there is less deformation of the underlying tissue compared to heat-based treatments, but evenly delivering light to the side of the optical fiber has a significant impact on the treatment effect.

Photothermal therapy, unlike low-level laser treatment or photodynamic therapy, uses high energy to deliver light energy to tissues, causing the chromophore within the tissues to absorb the light to increase the temperature, thereby inducing necrosis in diseases, tumor tissues, or the like. Light energy is first absorbed into the tissue, then heat is generated, raising the temperature, and as the heat is conducted to surrounding tissues, affecting the composition or combination of the tissue. Various biological changes occur depending on the temperature generated within the tissue. When the temperature is 42° C., a thermal effect and protein shrinkage occur, when the temperature is 50° C., a decrease in enzyme activity and slowing of cell movement occur, when the temperature is 60 to 70° C., protein denaturation and coagulation occur, when the temperature is 80° C. osmosis of cell membrane occurs, when the temperature is 100° C. vaporization, thermal decomposition, removal, and destruction occur, and when the temperature is above 100° C., dissolution, carbonization, and the like occur. In order to induce tissue changes as temperature rises, light energy must be delivered uniformly to ensure high treatment effectiveness and safety. Temperature rise (ΔT, ° C.) may be predicted by using [Equation 1], wherein $\mu_a$ is tissue absorption rate (1/cm), H is light energy per unit area (J/cm$^2$), ρ is tissue density (kg/cm$^3$), c is tissue specific heat (J/kgK). To increase the effect of photothermal therapy, light energy, pulse length, beam size, repetition rate, wavelength, and optical/thermal characteristics of tissues must be carefully considered and selected.

$$\Delta T=\mu_a H/\rho c \quad \text{[Equation 1]}$$

The present disclosure focuses on the above-described low-level light therapy, photodynamic therapy, and photothermal therapy methods and applies them to a light-based disinfection device, wherein the light-based disinfection device widely and uniformly radiates light, such as laser beams, near-ultraviolet rays, visible rays, and near-infrared rays, around a skin tissue where the drug is injected in close proximity to the injection needle during drug injection, thereby disinfecting the area where the skin tissue and the injection needle are in contact with each other, thereby minimizing and preventing infection. For example, when administering an anticancer drug by inserting an injection needle into the chemoport, the needle insertion site can be disinfected by applying the light-based disinfection device of the present disclosure in the vicinity of the needle, and the light-based disinfection device can also be applied to the surrounding transplanted tissues, which allows for extensive optical disinfection. In addition, infection around the chemoport can be prevented by performing periodic non-contact optical disinfection by applying the light-based disinfection device of the present disclosure during or after anticancer drug administration. In addition, it is expected that the light-based disinfection device of the present disclosure can be used in various implantable devices or the like.

FIG. 1 is a conceptual view of a light-based disinfection device 100 of the present disclosure.

Figure 2:
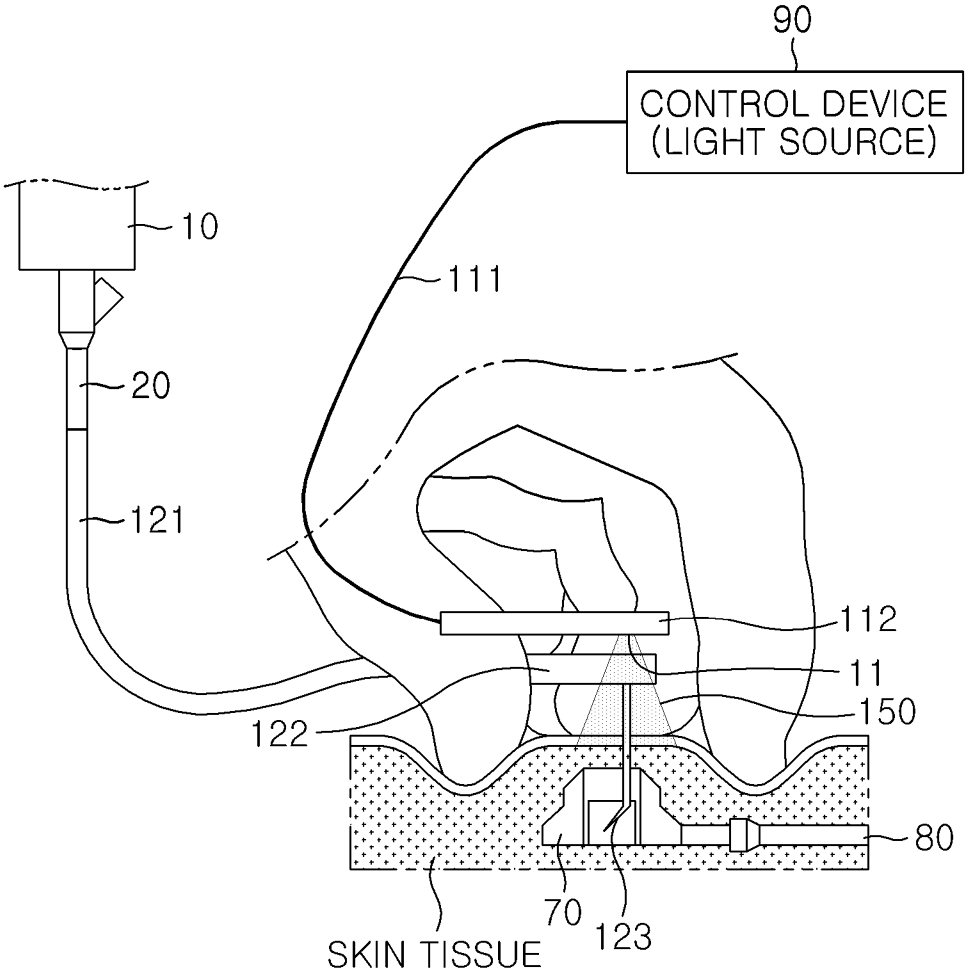
FIG. 2 is an example of applying the light-based disinfection device of the present disclosure to a chemoport.

FIG. 2 illustrates an example of applying the light-based disinfection device 100 of the present disclosure to the chemoport 70.

Referring to FIGS. 1 and 2, the light-based disinfection device 100 of the present disclosure, which disinfects a skin tissue by placing an injection needle 123 for drug injection and light 150 in close proximity, may include: a light delivery catheter 112 configured to direct the light 150 of a light source 11 controlled by a control device 90 to the skin tissue; a needle catheter 122 configured to accommodate a catheter line 121, which receives a drug from a drug container 10, such as an IV tube or syringe cylinder, and to administer the drug using the injection needle 123; and a coupler 130 configured to couple the light delivery catheter 112 and the needle catheter 122 to each other. The coupler 130 may be in the form of a connector or tube, and the light delivery catheter 112 and the needle catheter 122 may be coupled in parallel in the longitudinal direction by the coupler 130.

As illustrated in FIG. 2, when repeated drug administration is required for a long period of time, such as anticancer drug administration, the chemoport 70 may be inserted into a patient's body, such as the upper left subcutaneous fat layer of the patient, and the chemoport 70 may be connected to a catheter 80 inserted into a central vein. An injection needle 123 (e.g., Huber-point needle) is inserted into the chemoport 70 so that the drug in the drug container 10, such as an IV tube or syringe cylinder, can be injected into the patient's blood vessel. The drug container 10, such as an IV tube or syringe cylinder, may be connected to the catheter line 121 via a connector 20, allowing the drug to flow to the injection needle 123 through the needle catheter 122.

The catheter line 121 may be supported by being fixed to the patient's body, a surrounding holder, or the like via a clip 50. The light delivery catheter 112 and the needle catheter 122, which are coupled and fixed by the coupler 130, are fixed at a predetermined distance from the patient's body so as not to shake while the drug is administered to the patient through the injection needle 123. In order to ensure that the light delivery catheter 112 and the needle catheter 122 are fixed at a predetermined distance from the patient's body so as not to shake as described above, a fixation tool 60 may be used. The fixation tool 60 may be shaped to surround the light delivery catheter 112 and the needle catheter 122, and may be provided with an adhesive material (e.g., in the form of adhesive tape) attached to the patient's body, at least on its opposite sides.

Figure 3:
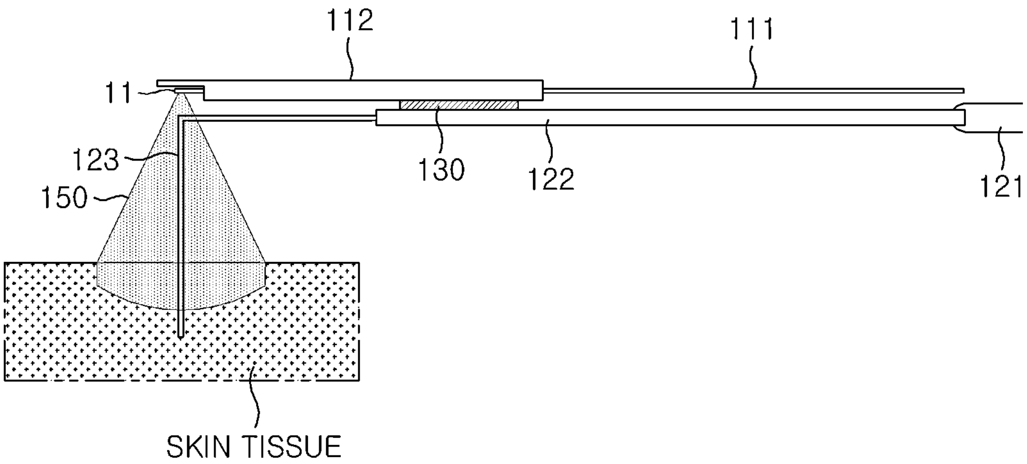
FIG. 3 is a view specifically illustrating a light delivery catheter and a needle catheter of the present disclosure.

FIG. 3 is a view specifically illustrating the light delivery catheter 112 and the needle catheter 122 of the present disclosure.

Referring to FIG. 3, the light delivery catheter 112 is connected to the control device 90 at one end portion, and directs the light 150 of the light source 11 controlled by the control device 90 at the other end portion toward the skin tissue. The needle catheter 122 is connected to the drug container 10 at one end portion and accommodates the catheter line 121 that provides the drug, and at the other end portion, the needle catheter 122 accommodates the injection needle 123 that receives the drug from the catheter line 121 and injects the drug into the patient's body.

Here, the light source 11 disposed at the other end portion of the light delivery catheter 112 may be an end portion of an optical fiber or an optical element. The optical device may be a variety of light-generating devices for optical disinfection, such as a light emitting diode (LED), a diode laser element, a pulsed laser element, a semiconductor laser element, and a diode pumped solid state (DPSS) laser device. When the optical element is placed at the other end portion of the light delivery catheter 112, the optical element may be connected to control lines and power lines 111 extending from the control device 90. When the optical element is placed in the control device 90, the light generated in the control device by the optical element may be delivered to the end portion of the optical fiber fixed to the other end portion via the optical fiber 111. The end portion of the optical fiber may be protected by being wrapped with an appropriate protective material that is effective in dissipating light.

Figure 9:
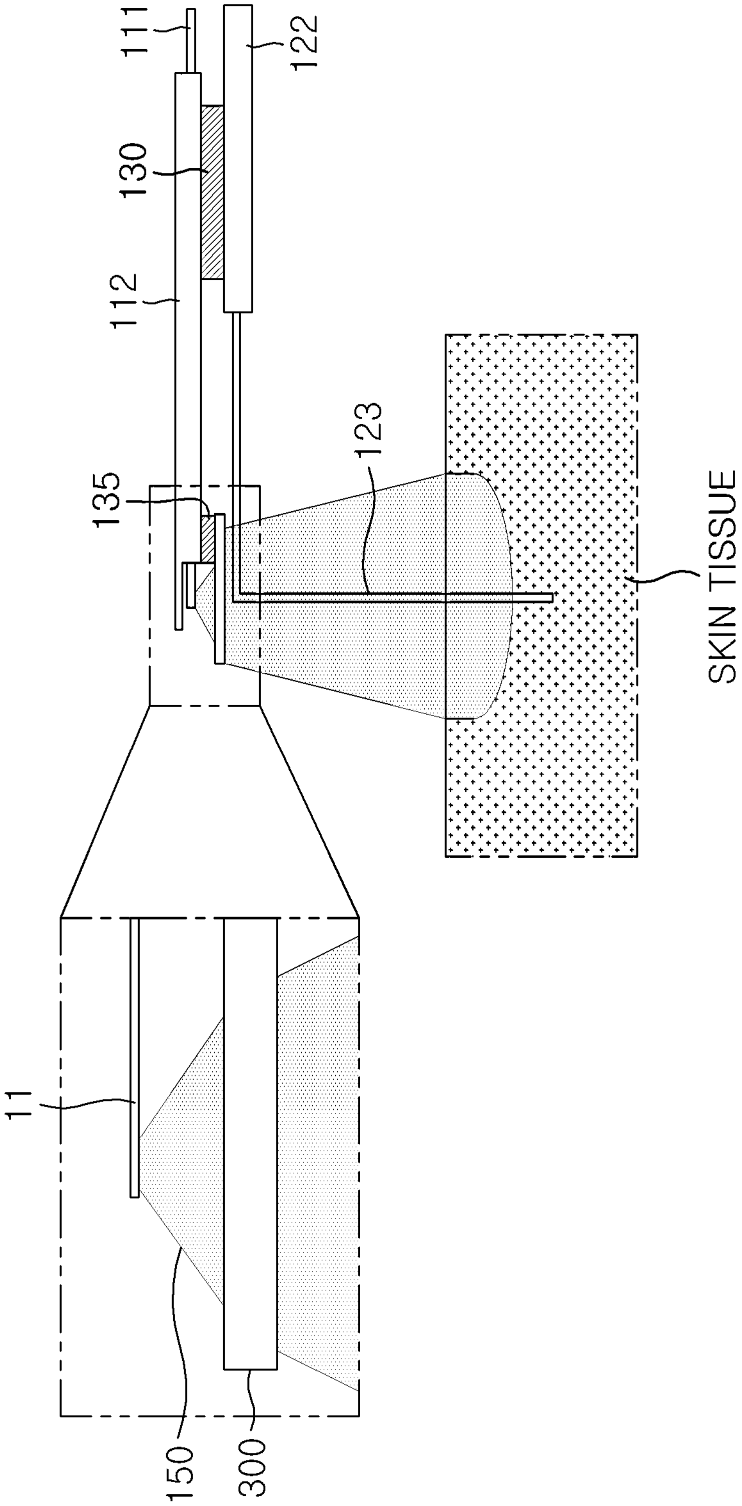
FIG. 9 is a view illustrating an example of use of a light radiation regulation portion that diffuses or scatters the light of the light delivery catheter of the present disclosure.

The light source 11 may emit laser beams, near-ultraviolet rays, visible rays, or near-infrared rays with a wavelength ranging from 400 nm to 3000 nm as continuous or pulsed light with an energy density ranging from 0.01 to 10 J/cm$^2$, and a power density ranging from 0.01 to 10 W/cm$^2$. Regarding the light source 11, under the control of the control device 90, one or more disinfection conditions may be controlled from among a light intensity (or selection in the above-mentioned wavelength range), a light emission time (variously applicable for, for example, 30 seconds to 10 minutes), selection of a continuous or pulsed light delivery method, an output energy or power range of the light (selection from the above energy/power density range), selection of a light distribution (whether optional use of the light radiation adjusting portion in FIG. 9 is possible), or the number of times of disinfection operation (e.g., the number of repetitions of light emission period). The control by the control device 90 may be performed according to user manipulation or software having a computer-readable code.

As illustrated in FIGS. 1 and 2, the above-mentioned control by the control device 90 may also be performed via a user terminal connected to the control device 90 via wired or wireless connection. Communication for the wired or wireless connection may be implemented in various ways, such as wired Internet communication, wireless Internet communication such as WiFi or WiBro, mobile communication such as WCDMA or LTE, or short-range wireless communication (e.g., Bluetooth, ZigBee, Wi-Fi, and the like). The user terminal may be a variety of terminals such as smartphones, laptop PCs, desktop PCs, and dedicated terminals.

Such a user terminal transmits the above-mentioned disinfection conditions or a schedule including one or more lists of the disinfection conditions stored in advance (e.g., disinfection conditions to operate in a predetermined order) to the control device 90 to control the operation of the light source 11. In addition, the user terminal may store information on the disinfection conditions or schedule which have been transmitted to the control device 90 and under which the operation of the light source 11 has been controlled, so that the corresponding information is provided in response to a user's inquiry request made in the future.

As illustrated in FIG. 3, when the light delivery catheter 112 and the needle catheter 122 are coupled in parallel to the longitudinal direction by the coupler 130, the coupler 130, for example, a connector-type coupler 130 may be configured to be rotatably disposed along the circumference of the light delivery catheter 112 or the needle catheter 122. Accordingly, the arrangement relationship of the light delivery catheter 112 and the needle catheter 122 may be appropriately placed in close proximity to the patient's body to properly direct the light 150 of the light source 11 to the skin tissue while maintaining the light delivery catheter 112 and the needle catheter 122 in parallel to each other. For example, the light delivery catheter 112 or the light source 11 at an end portion of the same may be placed above the needle catheter 122 or the injection needle 123 at the end portion of the same in the state in which the light delivery catheter 112 and the needle catheter 122 are parallel to each other.

As illustrate in FIG. 3, the end portion of the injection needle 123 may be curved or may be straight. As described below, in order to properly direct the light 150 of the light source 11 to the skin tissue, the light source 11 may be configured to be rotatable or bendable by using an appropriate mechanical member. In either case, the light 150 is preferably directed by the other end portion of the light delivery catheter 112 toward the end portion of the injection needle 123 at an angle of 30 to 90 degrees.

The light delivery catheter 112, the needle catheter 122, and the connector-type coupler 130 may be made of polytetrafluoroethylene (PTFE), polyethylene, polyvinyl chloride, nylon 66, 11, 12, urethanes, polyurethanes, polypropylene, polycarbonate, ABS, Pebax, polyetheretherketone (PEEK), or polyethylene terephthalate (PET).

Figure 4A:
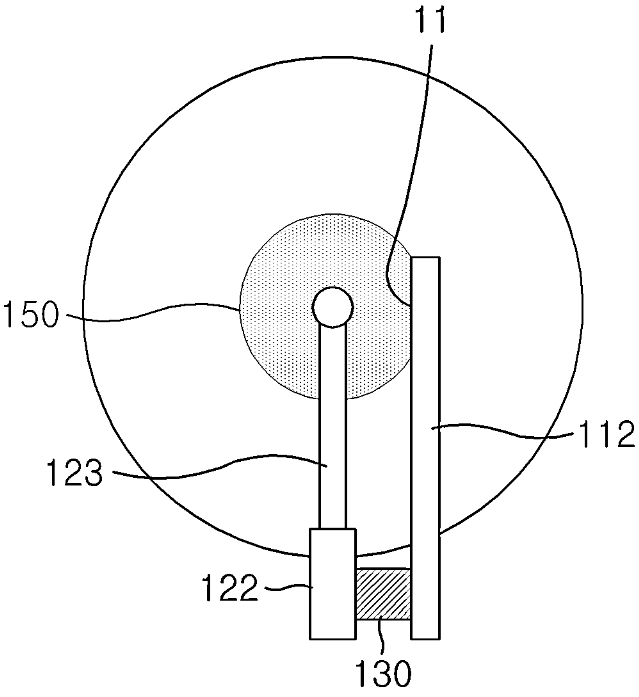
FIGS. 4A and 4B illustrate examples of the end portions of the light delivery catheter of the present disclosure.
Figure 4B:
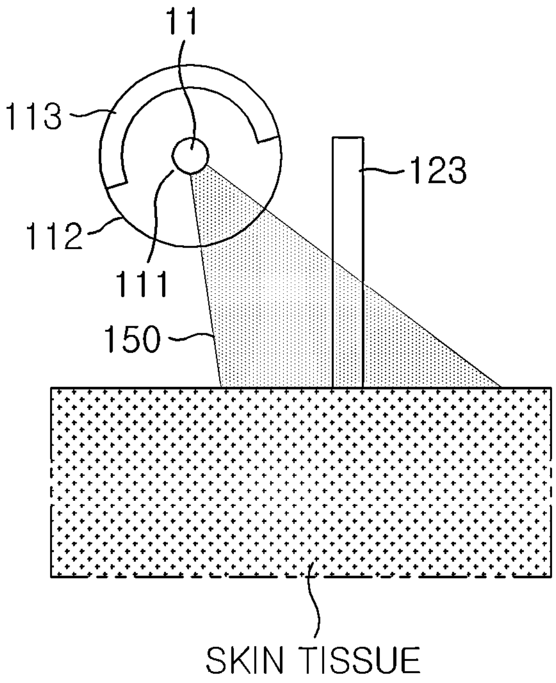

FIGS. 4A and 4B illustrate examples of the end portions of the light delivery catheter 112 of the present disclosure.

Referring to FIGS. 4A and 4B, for example, the light source 11 at the end portion of the light delivery catheter 112 may be placed higher or lower relative to the skin tissue than the injection needle 123 directed to the skin tissue while being appropriately spaced laterally relative to the injection needle 123 at the end portion of the needle catheter 122. The end portion of the injection needle 123 may be curved or may be straight. In order to properly direct the light 150 of the light source 11 to the skin tissue, the light source 11 may be configured to be rotatable or bendable by using an appropriate mechanical member. In either case, the light 150 is preferably directed by the other end portion of the light delivery catheter 112 toward the end portion of the injection needle 123 at an angle of 30 to 90 degrees.

As illustrated in FIG. 4B, a light diffusion prevention film 113 may be included at the other end portion of the light delivery catheter 112. The light diffusion prevention film 113 may direct the light from the light source 11 toward the skin tissue while blocking light that is reflected or scattered rearward after the light is radiated to the skin tissue, thereby avoiding unwanted stimulation. The light diffusion prevention film 113 may be mounted on a predetermined mechanical member configured to be rotatable or bendable around the light source 11 at the other end portion of the light delivery catheter 112, and may be manipulated to be appropriately placed on a side opposite to the skin tissue with respect to the light source 11 depending on the rotation or bending of the mechanical member.

Figure 5A:
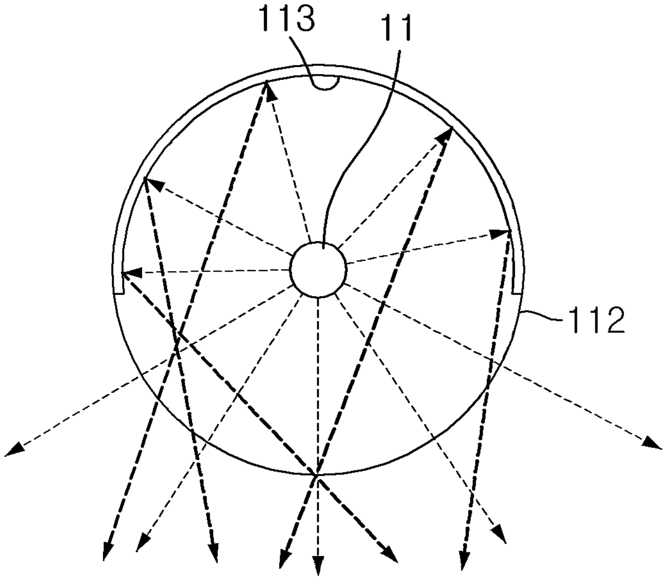
FIGS. 5A and 5B are views illustrating light diffusion prevention films of the present disclosure.
Figure 5B:
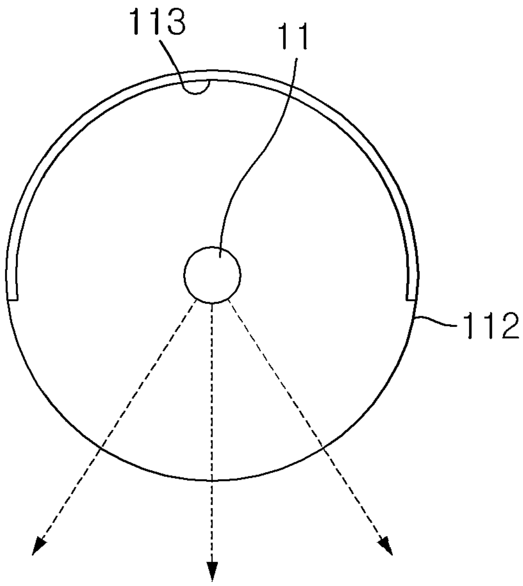

FIGS. 5A and 5B are views illustrating examples of the light diffusion prevention film 113 of the present disclosure of FIG. 4B.

Referring to FIG. 5A, the light diffusion prevention film 113 may include a coating film to reflect or scatter light. The coating film may be made of a material with a high reflectivity or a material that generates scattering. Accordingly, after the light is radiated to the skin tissue, the light reflected or scattered rearward can be radiated to the skin tissue again through reflection or scattering. Through this, the light reflected or scattered rearward may be blocked to avoid unwanted stimulation, and the skin tissue can be disinfected by the light reflected or scattered through the diffusion prevention film 113 simultaneously with the light directly radiated to the skin tissue by the light source 11.

Referring to FIG. 5B, the light diffusion prevention film 113 may include a coating film for absorbing light. The coating film may be made of a material with a high light absorption rate to allow the light from the light source 11 to be absorbed rather than reflected or scattered, thereby preventing the light from leaking rearward and thus avoiding unwanted stimulation. Therefore, when light is radiated, only the light emitted through the light source 11 and directly radiated to the skin tissue disinfects the skin issue, so that the light can be used to control disinfection conditions.

Figure 6A:
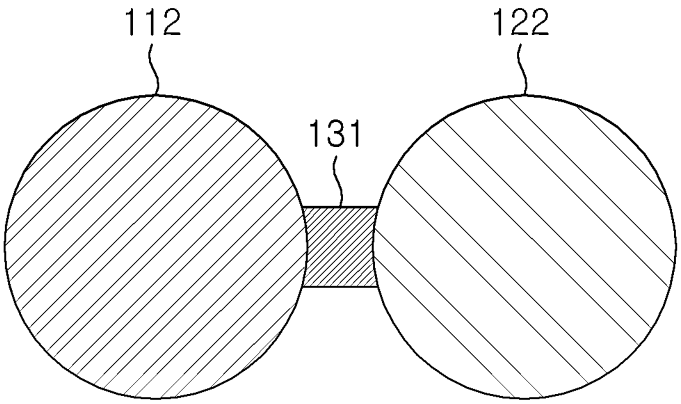
FIGS. 6A and 6B are views illustrating methods of coupling the light delivery catheter and the needle catheter of the present disclosure.
Figure 6B:
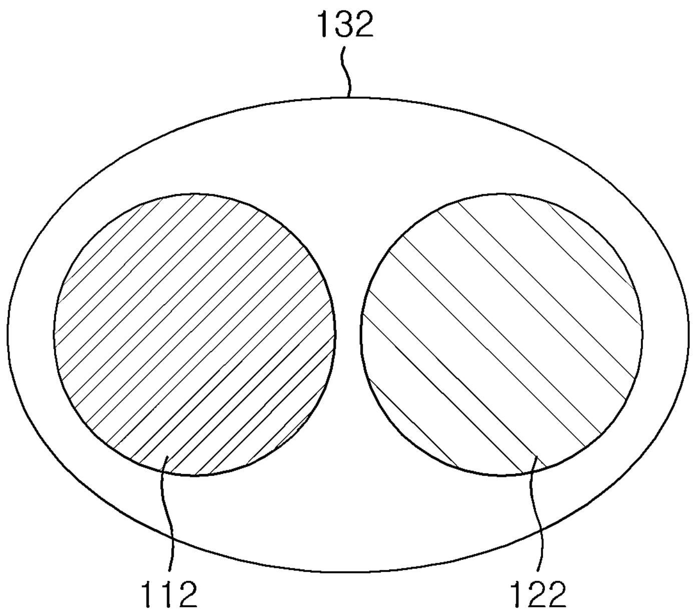

FIGS. 6A and 6B are views illustrating methods of coupling the light delivery catheter 112 and the needle catheter 122 of the present disclosure.

Referring to FIG. 6A, the coupler 130 may be a catheter connector 131 configured to be rotatably disposed around either the light delivery catheter 112 or the needle catheter 122. For example, the catheter connector 131 as the coupler 130 may be configured such that one side of the catheter connector can be fixed while surrounding part or all of the longitudinal body of either the light delivery catheter 112 or the needle catheter 122 and can be rotated and moved along the circumference of the body, and the other one of the light delivery catheter 112 and the needle catheter 122 can be fixed to the other side of the catheter connector. The other side of the coupler 130 may also be configured to be fixed while surrounding part or all of the circumference of the bodies 112 and 122 and to be rotatable along the circumference of the bodies.

Referring to FIG. 6B, the coupler 130 may be a tube 132 configured to be integrated with the light delivery catheter 112 and the needle catheter 122 by surrounding the bodies of the light delivery catheter 112 and the needle catheter 122 which are placed therein. For example, the tube 132 may be made of polytetrafluoroethylene (PTFE), polyethylene, polyvinyl chloride, nylon 66, 11, 12, urethanes, polyurethanes, polypropylene, polycarbonate, ABS, Pebax, polyetheretherketone (PEEK), or polyethylene terephthalate (PET).

Figure 7A:
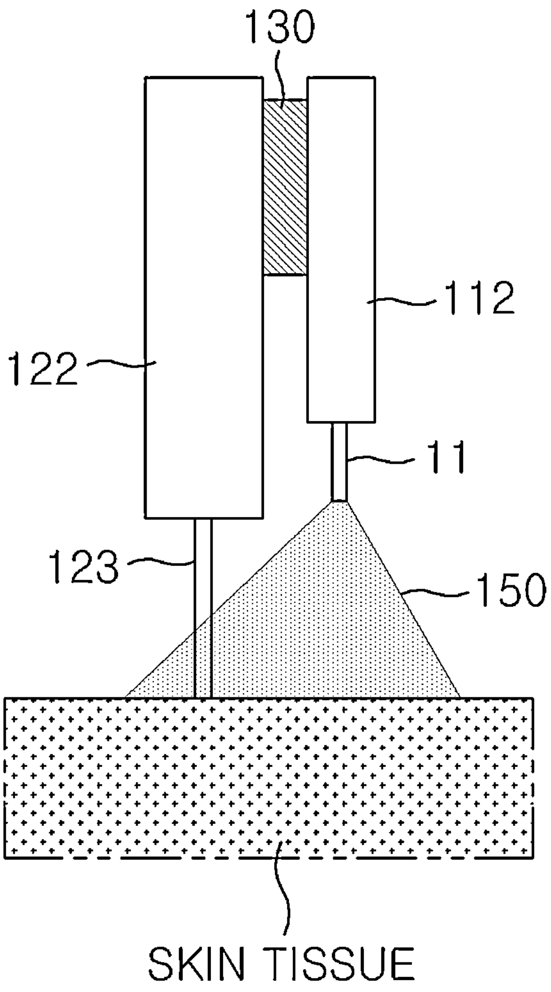
FIGS. 7A and 7B are views illustrating light radiation directions of the light delivery catheter depending on the extension shapes of the injection needle of the needle catheter of the present disclosure.
Figure 7B:
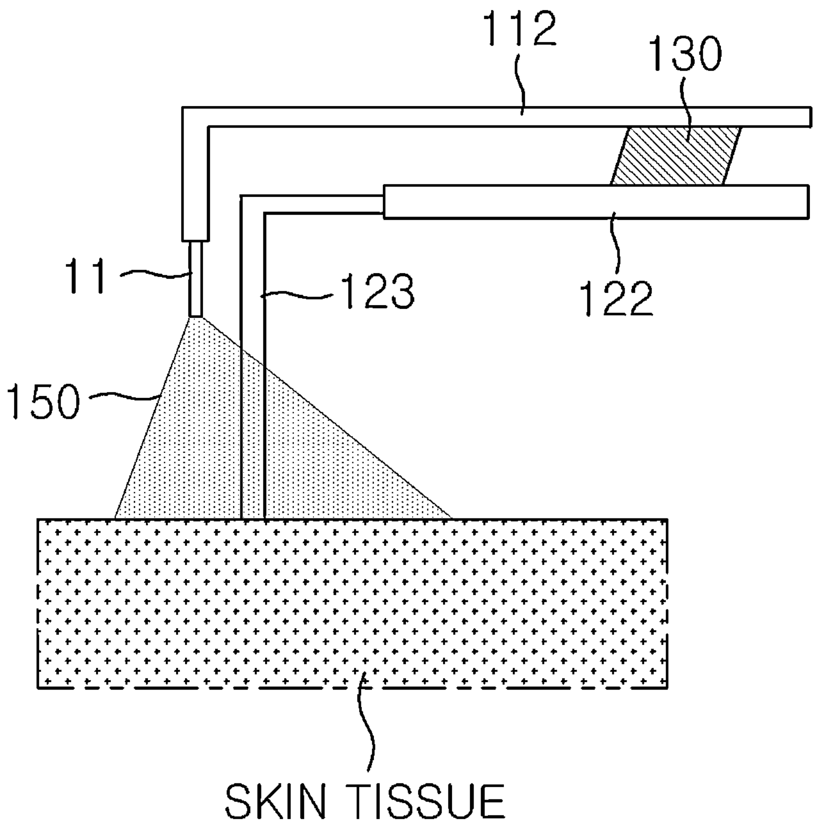

FIGS. 7A and 7B are views illustrating light radiation directions of the light delivery catheter 112 depending on the extension shapes of the injection needle 123 of the needle catheter 122 of the present disclosure.

Referring to FIG. 7A, when the injection needle 123 of the needle catheter 122 is extended and directed in the longitudinal direction of the needle catheter 122 (or when its end is inserted into skin tissue) for the administration of an anticancer drug or the like, the other end portion of the catheter 112 may be configured to extend in the extension direction without being bent, and the bodies of the light delivery catheter 112 and the needle catheter 122 may be arranged in parallel to each other with a separation distance of 0 to 5 mm therebetween. At this time, in order to ensure a disinfection rage, the light source 11 of the light delivery catheter 112 may be arranged to be directed at a predetermined angle (e.g., 10 to 30 degrees) toward the end portion of the injection needle 123 by the rotatable or bendable member, as described above.

Referring to FIG. 7B, when the end portion of the injection needle 123 at the other end portion of the needle catheter 122 is bent and directed in another direction at a right angle or a predetermined angle with respect to the longitudinal direction, the other end portion of the light delivery catheter 112 may also be bent in another direction at the right angle or the predetermined angle to direct the light 150 toward the skin tissue. At this time, in order to ensure a disinfection range, the light source 11 of the light delivery catheter 112 may be arranged to be directed at a predetermined angle (e.g., 10 to 30 degrees) toward the end portion of the injection needle 123 by the rotatable or bendable mechanical member, as described above. The angle of the radiated light 150 may be 30 to 90 degrees.

Although not illustrated in the drawing, when the end portion of the injection needle 123 at the other end portion of the needle catheter 122 is bent and directed in a different direction with respect to the longitudinal direction as described above, the other end portion of the light delivery catheter 112 may be extended in an extension direction without being bent. At this time, in order to secure the disinfection range, the light source 11 of the light delivery catheter 112 may be arranged to be directed toward the end portion of the injection needle 123 by the rotatable or bendable mechanical member. The angle of the radiated light 150 may be 30 to 90 degrees.

Figure 8A:
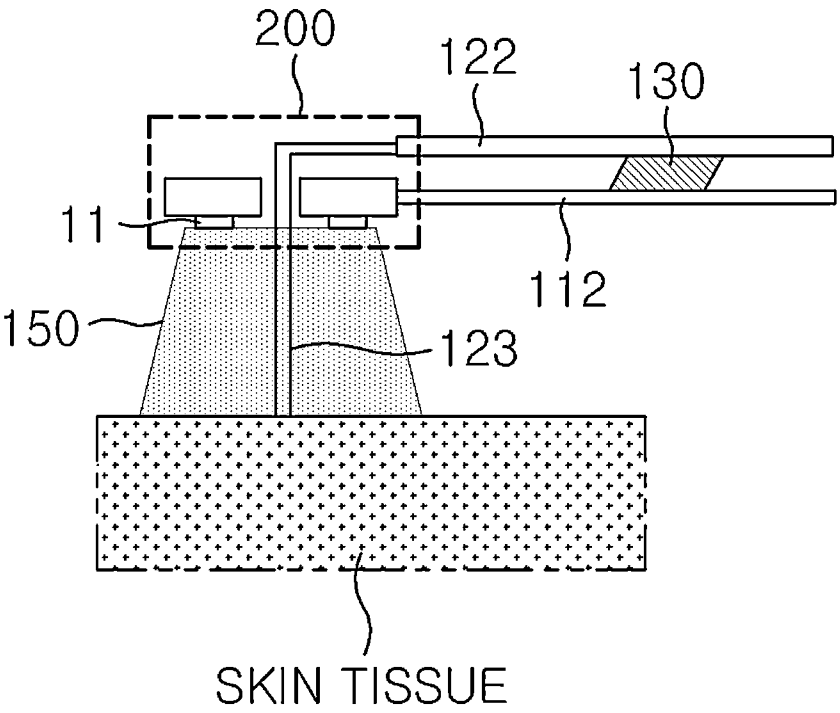
FIGS. 8A and 8B are views illustrating an example of using a plurality of light sources provided in a light radiation portion of the light delivery catheter of the present disclosure.
Figure 8B:
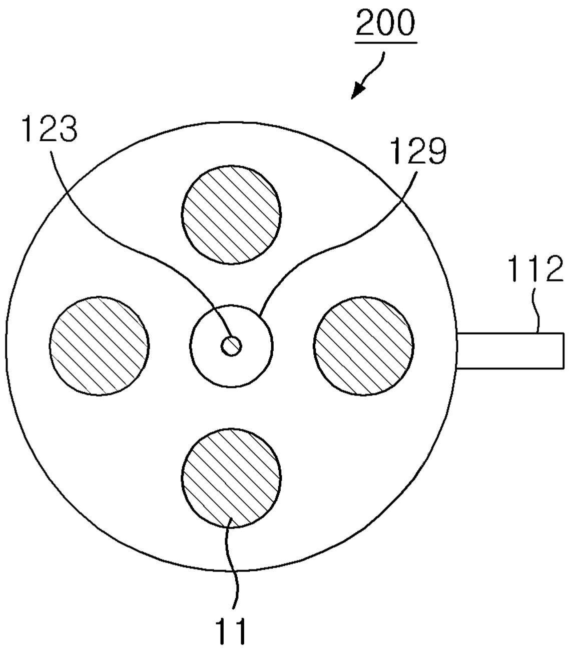

FIGS. 8A and 8B are views illustrating an example of using a plurality of light sources provided in a light radiation portion 200 of the light delivery catheter 112 of the present disclosure. FIG. 8B is a view illustrating the light radiation portion 200 of FIG. 8A when viewed from below.

Referring to FIGS. 8A and 8B, the light-based disinfection device 100 of the present disclosure may include a light radiation portion 200 including a housing having a hole 129 for inserting an injection needle 123 into the other end portion of the light delivery catheter 112. Here, a plurality of light sources 11 controlled by the control device 90 may be arranged around the hole 129 of the housing of the light radiation portion 200. The plurality of light sources 11 may be end portions of optical fibers that deliver light from the control device 90 via optical fibers, or may be optical elements such as LEDs as described above.

The light radiation portion 200 in which the plurality of light sources 11 are arranged may also be arranged to be directed toward the end portion of the injection needle 123 in the direction of a predetermined angle (e.g., 10 to 30 degrees) by the rotatable or bendable mechanical member. Light beams from the plurality of light sources 11 may be radiated to the skin tissue in an overlapping manner, or may be radiated to the skin tissue independently without overlapping. The plurality of light sources 11 may be configured such that each light source radiates light beams having the same wavelength, the light sources radiate light beams having different wavelengths from group to group, or all the light sources may radiate light beams having different wavelengths.

FIG. 9 is a view illustrating an example of use of a light radiation regulation portion 300 that diffuses or scatters the light of the light delivery catheter 112 of the present disclosure.

Referring to FIG. 9, the light-based disinfection device 100 of the present disclosure may further include a light radiation regulation portion 300 configured to diffuse or scatters the light 150 from the other end portion of the light delivery catheter 112 to adjust the light to have a predetermined light radiation range to the skin tissue (e.g., the total angle of the light-radiated range, the diameter of the light radiated area, or the like), light radiation intensity (e.g., wavelength or the like), or a light distribution.

In order to radiate the light 150 from the light source 11 to the skin tissue at a predetermined energy density during optical disinfection, the light radiation regulation portion 300 may be made of a light diffusion or scattering material or may have a layer of the material on the surface or inside a transparent material. Alternatively, when the light radiation regulation portion 300 is for diffusion, the light radiation regulation portion 300 may be provided with grooves on its surface (one side or both sides) continuously/discontinuously and symmetrically/asymmetrically to enable light diffusion. Alternatively, when the light radiation regulation portion 300 is for scattering, a scattering material (e.g., $SiO_2$, nano or micro particles, or the like) may be placed on or inside the transparent surface of the light radiation regulation portion 300.

Similar to detachably attaching the light delivery catheter 112 to the needle catheter 122 by using the catheter connector 130, the light radiation regulation portion 300 may be configured to be detachably attached to the other end portion of the light delivery catheter 112 by using an additional connector 135. The additional connector 135 may be configured to be rotatable along the circumference of the body of the light delivery catheter 112, and the light radiation regulation portion 300 may be configured to be rotatably or bendably coupled to the additional connector 135.

This light radiation regulation portion 300 may include respective elements for the above-mentioned functions, and in some cases where the disinfection conditions such as light radiation range, light radiation intensity, and light distribution are selected under the control of the control device 90, the corresponding elements of the light radiation regulation portion 300 may be selected so that disinfection can be performed. The selection of the corresponding elements of the light radiation regulation portion 300 may be made automatically under electronic control, or may be manually performed by a user by displaying the corresponding information on a display device such as an LCD or LED to notify the user of the information.

Figure 10:
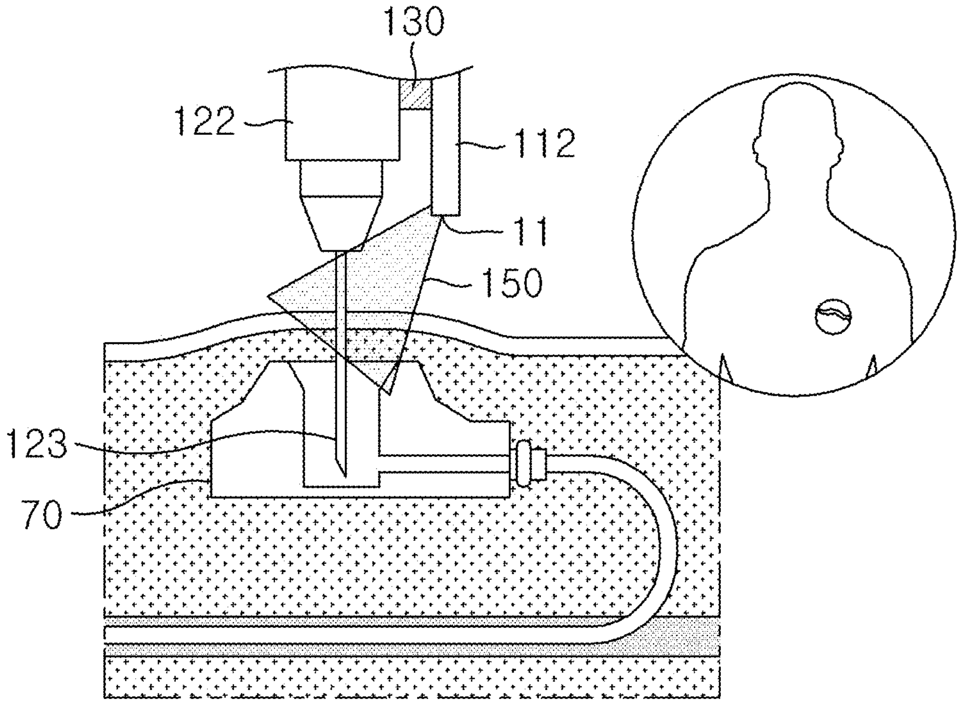
FIG. 10 is a view illustrating light radiation when the injection needle of the needle catheter of the present disclosure is used vertically.

FIG. 10 is a view illustrating light radiation when the injection needle 123 of the needle catheter 122 of the present disclosure is used vertically.

Referring to FIG. 10, when the injection needle 123 of the other end of the needle catheter 122 extends in the extension direction without being bent, the light source 11 fixed to the other end portion of the light delivery catheter 112 may be configured to be rotatable or bendable by a predetermined mechanical member or element so that the direction of light radiation can be changed.

For example, when the injection needle 123 is inserted vertically when administering an anticancer drug, it is possible to optically disinfect the site where the injection needle 123 is inserted into the skin tissue and the surrounding tissue at a predetermined distance from the site at the same time by placing the light delivery catheter 112 in parallel to the needle catheter 122 and bending the end portion of the light delivery catheter 112 by a predetermined angle or by forming the light radiation direction from the light source 11, such as an optical fiber, at a predetermined angle.

Figure 11A:
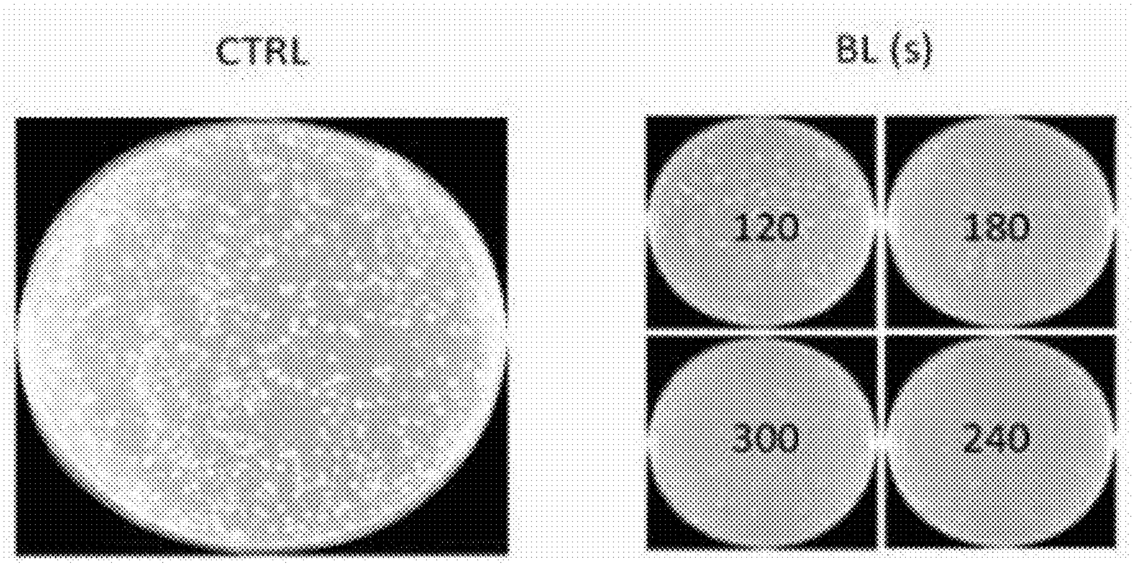
FIGS. 11A, 11B and 11C are views illustrating the results of an experiment on the effect of optical disinfection on pseudomonas bacteria by the light-based disinfection device of the present disclosure.
Figure 11B:
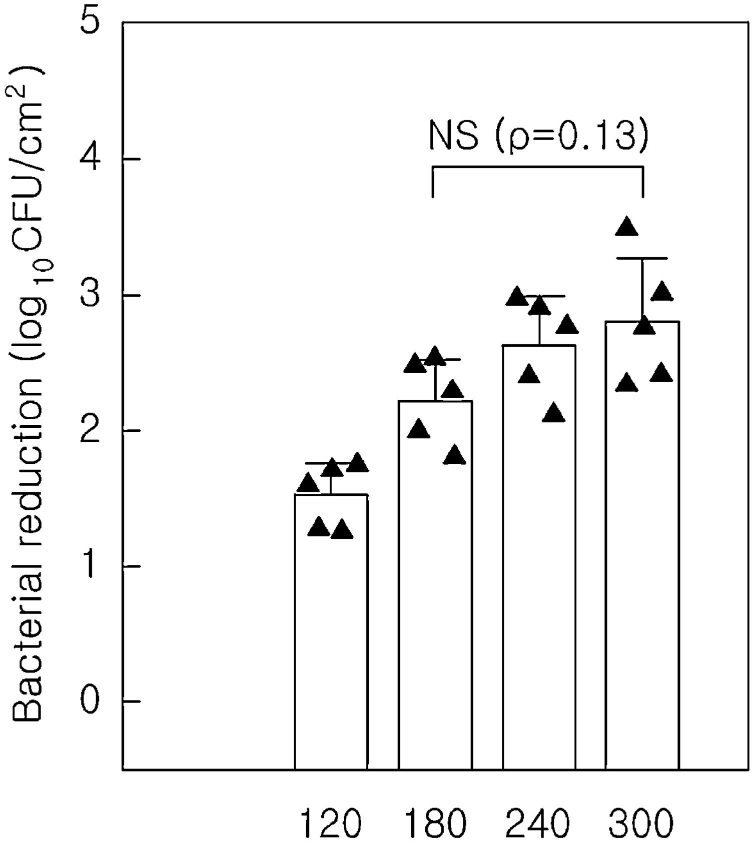
Figure 11C:
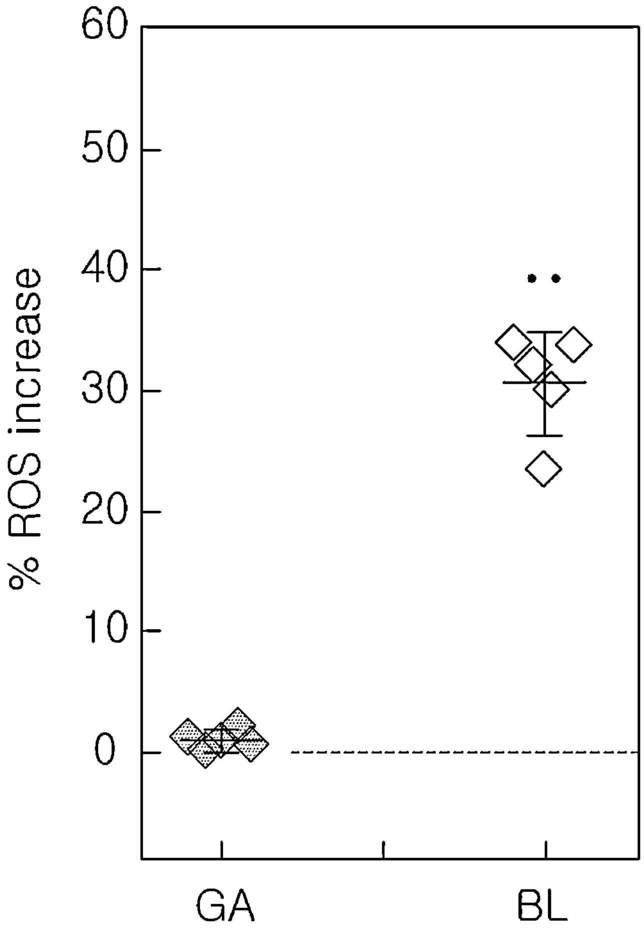

FIGS. 11A to 11C are views illustrating the results of an experiment on the effect of optical disinfection on pseudomonas bacteria by the light-based disinfection device 100 of the present disclosure.

FIG. 11*a* illustrates a control group CTRL in which many pseudomonas bacteria remain, and illustrates relative increases in energy density (e.g., 120, 180, 240, and 300) for optical disinfection (e.g., by a blue laser (BL) with a wavelength of 405 nm) by the light-based disinfection device 100 of the present disclosure for application thereto.

As illustrated in FIG. 11*b*, the measurement of bacterial clusters remaining per unit area (log CFU/$m^2$) after optical disinfection by the light-based disinfection device 100 of the present disclosure as described above revealed a significant decrease in bacterial clusters as energy density increased, indicating a linear decrease on a logarithmic scale. The p value indicating that there is no significant difference (NS: not statistically significant) in the hypothesis of the statistical test can be supported by the result of 0.13 (there is a difference).

As noted from FIG. 11C, it has been confirmed that compared to a disinfectant (glutaraldehyde) GA used for bacterial disinfection, a large amount of reactive oxygen species (ROS) was generated when applying the above-described optical disinfection BL of the present disclosure. Therefore, it was confirmed that the increase in active oxygen generated from bacteria upon light radiation is the main mechanism for optical disinfection of bacteria.

Figure 12A:
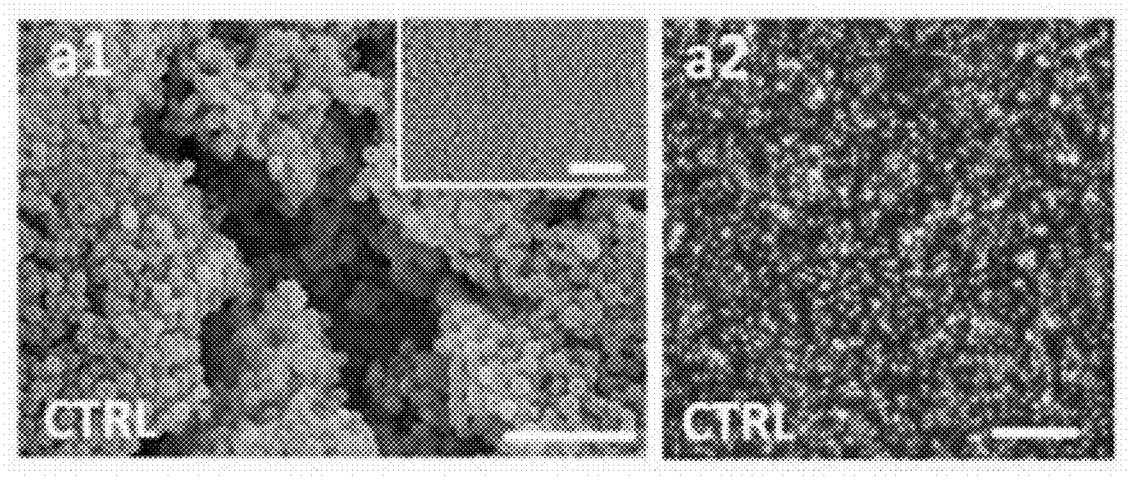
FIGS. 12A and 12B are images of bacteria taken with an electron microscope (left) and a fluorescence microscope (right) before and after light-based disinfection of pseudomonas by the light-based disinfection device of the present disclosure.
Figure 12B:
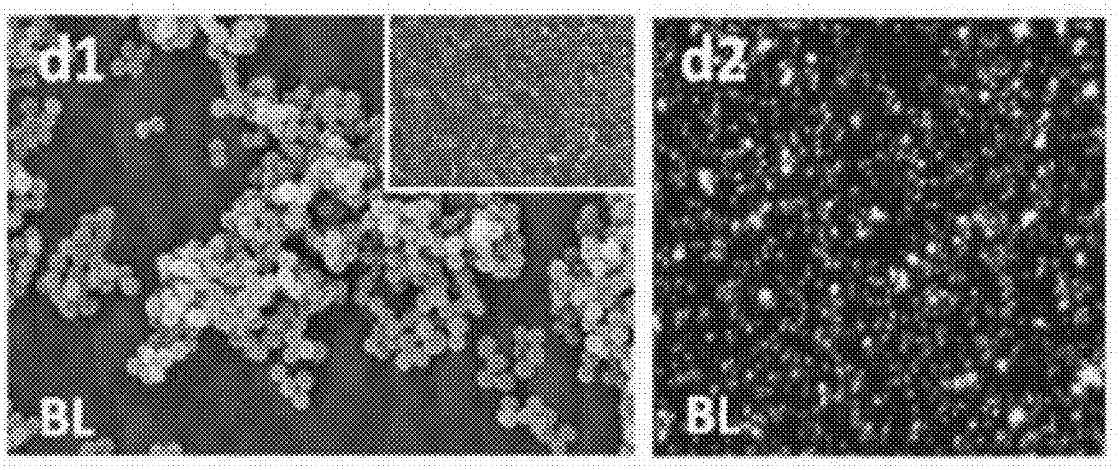

FIGS. 12A and 12B are images of bacteria taken with an electron microscope (left) and a fluorescence microscope (right) before and after light-based disinfection of pseudomonas by the light-based disinfection device 100 of the present disclosure. In FIG. 12A, the image a2 is an enlarged image of a portion of the image a1, and in FIG. 12B, the image d2 is an enlarged image of a portion of the image d1 at the same magnification.

As illustrated in FIG. 12A, it was confirmed that a large amount of bacteria was present in a control group CTRL, and, as illustrated in FIG. 12B, it was confirmed that when the above-described optical disinfection of the present disclosure BL was applied, the number of bacteria decreased.

As described above, with the light-based disinfection device 100 of the present disclosure, during drug injection, it is possible to minimize and prevent infection by radiating light such as laser beams, near-ultraviolet rays, visible rays, or near-infrared rays widely and uniformly around the skin tissue in close proximity to the injection needle 123 during drug injection to ensure that the site where the skin tissue and the injection needle 123 are in contact with each other and the surroundings of the site are disinfected. For example, when administering an anticancer drug by inserting the injection needle 123 into the chemoport 70, the site where the injection needle 123 is inserted and its surroundings can be disinfected by applying the light-based disinfection device 100 of the present disclosure around the injection needle 123, and the light-based disinfection device can also be applied to the surrounding transplanted tissues, which allows for extensive optical disinfection. In addition, infection around the chemoport 70 can be prevented by performing periodic non-contact optical disinfection by applying the light-based disinfection device 100 of the present disclosure during or after anticancer drug administration. In addition, it is expected that the light-based disinfection device 100 of the present disclosure can be used in various implantable devices or the like.

As described above, the present disclosure has been described based on specific details, such as specific components, limited embodiments, and drawings, but these are only provided to help a more general understanding of the present disclosure, and the present disclosure is not limited to the above-described embodiments. A person ordinarily skilled in the art to which the present disclosure pertains may make various modifications and changes without departing from the essential characteristics of the present disclosure. Therefore, the spirit of the present disclosure should not be limited to the described embodiments, and not only the appended claims, but also all technical ideas equivalent to or equivalently modified to the claims should be interpreted as being included in the scope of the present disclosure.

What is claimed is:

1. A light-based disinfection device configured to achieve disinfection of a skin tissue by placing light in close proximity to a separate injection needle for drug injection, the light-based disinfection device comprising:

a light delivery catheter comprising one end portion connected to a control device and a remaining end portion configured to direct light from a light source controlled by the control device toward the skin tissue, and a light diffusion prevention film at the remaining end portion that blocks light reflected or scattered rearward when the light from the light source is radiated to the skin tissue, wherein the light diffusion prevention film is configured to be rotatable or bendable around the light source;

a connector rotatable along a circumference of a body of the light delivery catheter;

a light radiation regulation portion coupled to the connector and configured to regulate the light irradiated toward the skin tissue by diffusing or scattering the light from the remaining end portion of the light delivery catheter;

a needle catheter comprising one end portion connected to a drug container and to accommodate a catheter line that supplies a drug, and a remaining end portion configured to accommodate a separate injection needle that receives the drug from the catheter line and injects the drug into a patient's body; and a coupler configured to couple the light delivery catheter and the needle catheter, wherein the coupler is rotatable along the circumference of either the light delivery catheter or the needle catheter.

2. The light-based disinfection device of claim 1, wherein the light-based disinfection device is configured to insert the separate injection needle of the needle catheter into a chemoport inserted into the patient's body.

3. The light-based disinfection device of claim 1, wherein the light source comprises an optical element disposed at the remaining end portion of the light delivery catheter to be connected to control lines and power lines extending from the control device.

4. The light-based disinfection device of claim 1, wherein the light source comprises an optical fiber that delivers light generated by the control device and has an end portion disposed at the remaining end portion of the light delivery catheter.

5. The light-based disinfection device of claim 1, wherein the light source is configured to emit laser beams, near-ultraviolet rays, visible rays or near-infrared rays as continuous or pulsed light with a wavelength ranging from 400 nm to 3000 nm and an energy density of 0.01 to 10 J/cm$^2$, and power density of 0.01 to 10 W/cm$^2$.

6. The light-based disinfection device of claim 1, wherein the light source is configured to be controlled by the control device in terms of one or more disinfection conditions from among a light intensity, a light emission time, selection of a continuous or pulsed light delivery method, a light output energy or power range, selection of a light distribution, and a number of times of disinfection operation.

7. The light-based disinfection device of claim 6, further comprising:

a user terminal connected to the control device in a wired or wireless manner, wherein the user terminal is configured to:

control operation of the light source by transmitting the disinfection conditions or a schedule comprising one or more lists of the disinfection conditions stored in advance to the control device, store information on the disinfection conditions or the schedule used to control operation of the light source, and provide the stored information in response to a user's inquiry request.

8. The light-based disinfection device of claim 1, wherein the remaining end portion of the light delivery catheter is configured to radiate light toward an end of the separate injection needle at an angle of 30 to 90 degrees.

9. The light-based disinfection device of claim 1, wherein the light diffusion prevention film comprises a coating film configured to reflect or scatter light.

10. The light-based disinfection device of claim 1, wherein the light diffusion prevention film comprises a coating film configured to absorb light.

11. The light-based disinfection device of claim 1, wherein the coupler comprises a catheter connector configured to be placed and rotated around the light delivery catheter or the needle catheter.

12. The light-based disinfection device of claim 1, wherein the coupler comprises a tube configured to wrap bodies of the light delivery catheter and the needle catheter to place the bodies of the light delivery catheter and the needle catheter therein.

13. The light-based disinfection device of claim 1, wherein when an end portion of the separate injection needle at the remaining end portion of the needle catheter is bent and directed in a different direction with respect to a longitudinal direction, the remaining end portion of the light delivery catheter extends in an extension direction without being bent.

14. The light-based disinfection device of claim 1, wherein, when an end portion of the separate injection needle at the remaining end portion of the needle catheter is bent and directed in a different direction with respect to a longitudinal direction, the remaining end portion of the light delivery catheter is bent in the other direction to direct the light toward the skin tissue.

15. The light-based disinfection device of claim 1, wherein, when the separate injection needle at the remaining end portion of the needle catheter extends in an extension direction without being bent, the light source disposed at the remaining end portion of the light delivery catheter is configured to be rotatable or bendable such that a light radiation direction can be changed.

16. The light-based disinfection device of claim 1, wherein the remaining end portion of the light delivery catheter comprises a light radiation portion having a hole for inserting the injection needle, and wherein the light source comprises a plurality of light sources, controlled by the control device, which are arranged around the hole of the light radiation portion.

17. The light-based disinfection device of claim 1, further comprising:

the light radiation regulation portion is configured to regulate the light to have a predetermined light radiation range, light radiation intensity, or light distribution on the skin tissue.

* * * * *